United States Patent [19]

Skala

[11] Patent Number: 4,646,068

[45] Date of Patent: Feb. 24, 1987

[54] ICE MONITORING SYSTEM USING NEUTRON MODERATION

[76] Inventor: Stephen F. Skala, 3839 S. Wenonah Ave., Berwyn, Ill. 60402

[21] Appl. No.: 637,618

[22] Filed: Aug. 3, 1984

Related U.S. Application Data

[63] Continuation-in-part of Ser. No. 340,809, Jan. 19, 1982, abandoned.

[51] Int. Cl.⁴ .............................................. G08B 21/00
[52] U.S. Cl. .................................... 340/580; 250/392; 250/390; 324/71.3
[58] Field of Search ................ 340/580; 250/392, 391, 250/390 E, 308; 324/71.3; 73/170 R

[56] References Cited

U.S. PATENT DOCUMENTS

| | | | |
|---|---|---|---|
| 2,967,937 | 1/1961 | McKay | 250/390 |
| 3,621,714 | 11/1971 | Puccinelli | 73/170 R |
| 3,838,281 | 9/1974 | Dean et al. | 250/308 |
| 4,039,809 | 8/1977 | Bailey | 250/391 |

Primary Examiner—Glen R. Swann, III
Attorney, Agent, or Firm—Stephen F. Skala

[57] ABSTRACT

A layer of hydrogenous material, such as ice which may accumulate on an outer airplane surface, is monitored according to neutron moderation by the layer.

A source of fast neutrons and a detector of slow neutrons are mounted on one side of a mounting plate which may be the skin of an airplane. As a layer of ice or other hydrogenous material accumulates on the outer surface of the mounting plate, some of the fast neutrons collide with hydrogen nuclei therein to lose energy and be scattered into the slow neutron detector where each detected slow neutron generates an electrical pulse. The electrical pulses are transformed into a signal which corresponds to the amount of hydrogenous material per unit area.

4 Claims, 1 Drawing Figure

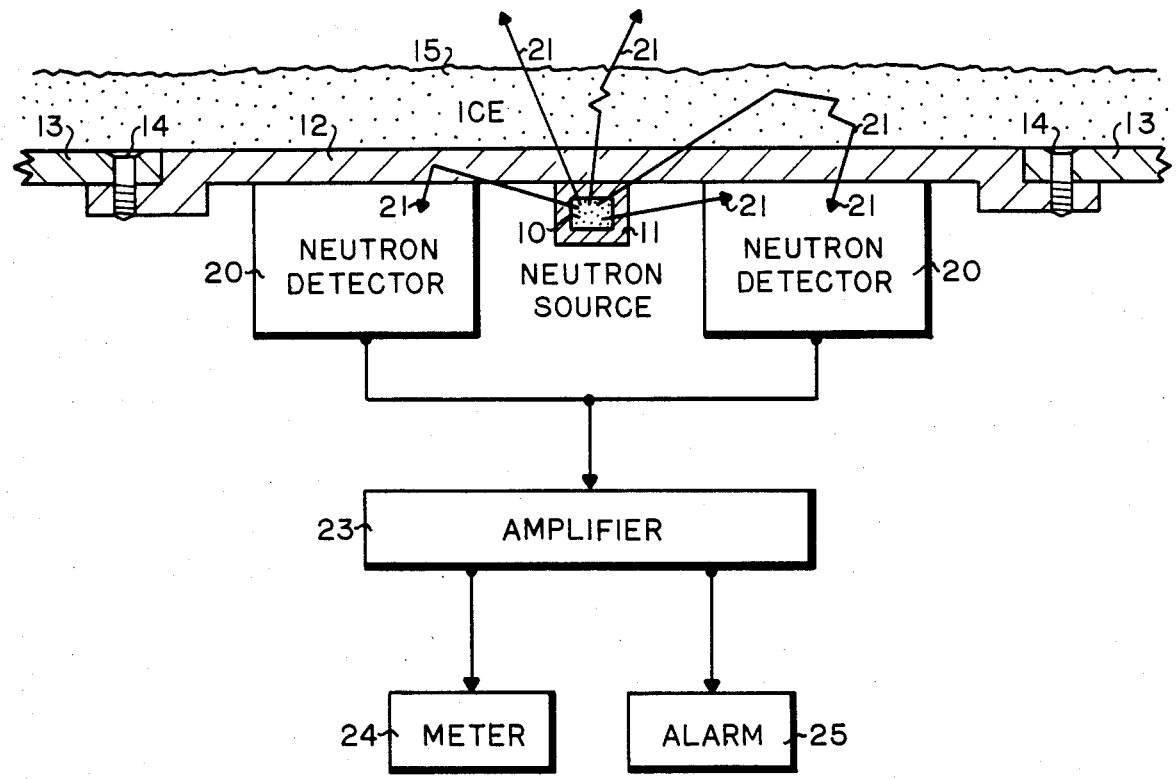

ICE MONITORING SYSTEM USING NEUTRON MODERATION

The present application is a continuation-in-part of application Ser. No. 340,809 filed Jan. 19, 1982 and now abandoned.

BACKGROUND

This invention relates to measurement of a layer of ice or other hydrogenous material and particularly to such measurement based on neutron moderation.

In the process of neutron moderation, fast neutrons collide with nuclei to loose energy and to be scattered. The most effective neutron moderator is a hydrogen nucleus which has almost the same mass as a neutron to result in a high rate of momentum transfer. Accordingly hydrogenous materials, such as ice which consists of $H_2O$ molecules, are much more effective for reducing the energy of fast neutrons than are other materials which may be present. Correspondingly, the number of slow neutrons can represent information on the presence of proximate hydrogen nuclei and this information can be enhanced statistically by reducing the extraneous noise of fast neutrons. A measuring system for proximate hydrogen nuclei based on neutron moderation would include a source of fast neutrons and a selective detector of slow neutrons.

A convenient source of fast neutrons is a radium-beryllium mixture in which the radium is a source of alpha particles which react with beryllium to produce fast neutrons in the following nuclear reaction:

$$_4Be^9 + _2He^4 \rightarrow _6C^{12} + _0n^1.$$

Conventional detectors of slow neutrons are based upon alpha emission from boron which occurs when the boron captures a slow neutron in the following nuclear reaction:

$$_5B^{10} + _0n^1 \rightarrow _3Li^7 + _2He^4.$$

The alpha particle actuates a charged particle detector. The boron provides selective detection of slow neutrons since its neutron capture cross section is much larger for slow than for fast neutrons.

Alternative nuclear reactions for producing fast neutrons and detecting slow neutrons with related apparatus in a backscatter configuration may be found in U.S. Pat. No. 4,039,809 issued to S. M. Bailey. Although this gage shares many components with the present invention, its use for measuring the varying hydrogenous composition of substantially constant configuration of a bulk material differs from the measurement of a varying basis weight or thickness of a layer of material having a constant hydrogenous composition. Further, the prior Bailey gage is not structured for mounting to the skin of an airplane for measuring accumulation of a layer of ice.

A radiation gage for monitoring ice accumulation on aircraft with circuits to process signals for indication, warning, and de-icing is disclosed Dean et al. in U.S. Pat. No. 3,838,281. The gage, however, is of the transmission type where components are undesirably located on the outer surface of an airplane skin. Further, alternative types of radiation do not share with moderated neutron systems the selective discrimination against background radiation from the source and from scattering by aircraft structures. Such background radiation reduces accuracy.

OBJECTS OF THE INVENTION

It is an object to provide an accurate gage for measuring basis weight or thickness of layers of hydrogenous materials.

It is another object to provide such a gage which is suitable for use on aircraft for measuring the basis weight or thickness of an accumulated layer of ice.

SUMMARY

These and other objects and advantages which will become apparent are attained by the invention wherein a gage based on neutron moderation in a backscatter configuration is used for measuring a variable basis weight or thickness of a layer of a hydrogenous material such as ice. The internal location of components associated with the backscatter configuration, including a source of fast neutrons and a detector of slow neutrons, is particularly suitable for use on aircraft to provide reliability and absence of aerodynamic drag. Yet mounting the internal components on a mounting plate which is attached to an airplane skin enables convenient access to the internal components. The use of neutron moderation with selective detection of slow neutrons results in a low background rate when ice is not present to provide a high sensitivity for thin layers thereby enabling indication of early ice formation. This sensitivity is also useful for general meterorological applications of the ice gage. The gage may include circuits of the type disclosed by Dean et al. for indication, warning, and control of de-icing on aircraft. It may also include the neutron sources and detector disclosed by Bailey. These and other known circuits, neutron sources, and detectors can be adapted to the use of measuring layers of ice, particularly on aircraft, according to the invention.

As ice accumulates on the aircraft surface to which the present ice gage is fastened, detection of slow neutrons increases. The quantity which affects the neutron detection rate is the number of hydrogen nuclei per unit area which corresponds directly to the weight per unit area which is the basis weight of the layer of ice. Ice thickness can be inferred from its basis weight when the density is known.

Gaging of ice on aircraft would be useful for both safety and economy. The increased weight and loss of lift due to ice formation have resulted in serious accidents. Ice can be removed before take-off by washing the aircraft with a de-icing solution but this is time consuming and costly. An accurate measurement of ice accumulation is needed to assure that ice is removed when necessary but that costly de-icing operations are not used otherwise. In flight, detection of ice accumulation can alert the pilot to a hazard and automatically initiate de-icing heaters and other apparatus.

BRIEF DESCRIPTION OF THE DRAWING

The drawing is a schematic diagram of a gage based on neutron moderation in a backscatter configuration used for measuring basis weight or thickness of a layer of hydrogenous material such as ice according to the invention. A source of fast neutrons and a detector of slow neutrons are on an inside surface of a mounting plate having an outside surface flush with an airplane skin. A layer of ice is shown on the outside surface.

DESCRIPTION OF THE PREFERRED EMBODIMENT

A source of fast neutrons 10 is encapsulated in a metal container 11 brazed to mounting plate 12 which is attached to an airplane skin 13 by screws 14. The outer surfaces of the mounting plate 12 and the airplane skin 13 are substantially flush. A layer of ice 15 may accumulate upon the mounting plate and the airplane skin. One or more detectors of slow neutrons 20 are attached to the mounting plate 12 and comprise a thin layer of boron adjacent to a charged particle detector which detects the alpha particles produced by a neutron-alpha reaction in the boron. The alpha particles which enter active portions of the detector generate an electrical amplitude which may consist of current or voltage pulses.

Fast neutrons are emitted in all directions by the source of fast neutrons 10 and may be scattered and moderated by the ice 15 and various nearby structures to travel in trajectories such as are suggested by lines 21. When the ice 15 is not present, almost all of the neutrons which enter the detectors 20 are fast since elements of higher atomic mass are ineffective moderators and the fast neutrons have a low probability of capture by the boron. Those which are detected contribute to a substantially constant background level of pulses from the detectors. As ice 15 accumulates, fast neutrons are moderated effectively to low energies by its hydrogen nuclei and are scattered into detectors 20 where they may be captured and detected. The number of neutrons which are moderated and detected increases with increasing ice basis weight and the relationship is similar to that shown for moisture concentration in the cited Bailey patent. Amplifier 23 is connected to receive voltage or current pulses from the detectors 20 and to transform the pulses into a signal which corresponds to ice basis weight or thickness by known digital or analogue means. This signal is transmitted to indicating meter 24 and to alarm assembly 25 which alerts the pilot to excessive ice accumulation. The alarm assembly 25 may also transmit a signal to a controller, not shown, for automatic control of de-icing apparatus.

In a digital system, pulses from the detectors 20 are counted over a time interval which is predetermined along with intensity of the source of fast neutrons for sufficiently frequent updating of icing conditions and for sufficient accuracy. The accuracy is $\pm 1/\sqrt{n}$ where n is the number of neutrons detected in the time interval. The amplifier includes a monostable flip-flop to shape the pulses from the detector, a scaler to count the pulses over the predetermined time interval, a computer to transform the counts into a number which is equivalent to the basis weight of an accumulated layer of ice, and the meter which displays the basis weight. The alarm includes a comparator to determine if the basis weight is above a reference value.

What I claim is:

1. A process for measuring basis weight of a layer of a hydrogenous material, comprising the steps of:

mounting a source of fast neutrons and a detector of slow neutrons proximate to each other on one side of a mounting plate whereby the fast neutrons are moderated and scattered by the layer of hydrogenous material which is proximate to the other side of the mounting plate and detecting a portion of the moderated and scattered noutrons by the detector whereby an electrical amplitude corresponding to the basis weight of the hydrogenous material is generated for measurement thereof.

2. The process of claim 1 wherein the layer of hydrogenous material is a layer of ice.

3. The process of claim 2 wherein the mounting plate is installed to be substantially flush with an outer surface of an airplane skin.

4. Apparatus for measuring a layer of ice which may accumulate on an airplane skin, comprising:

a mounting plate having an inside surface to which a source of fast neutrons and a detector of slow neutrons are attached, said mounting plate having means for attaching to an airplane skin whereby a layer of ice may accumulate on the outer surface of the mounting plate thereby moderating the fast neutrons for scattering into the detector and generating an output corresponding to the moderated neutrons entering the detector and means for transforming the output of the detector into a signal corresponding to the basis weight of the layer of ice.

* * * * *